(12) United States Patent
Pageon et al.

(10) Patent No.: US 6,890,754 B2
(45) Date of Patent: May 10, 2005

(54) EPIDERMIS/DERMIS EQUIVALENTS AND AGED SKIN EQUIVALENTS SHAPED THEREFROM

(75) Inventors: Hervé Pageon, Montgeron (FR); Daniel Asselineau, Antony (FR); Pierre Tachon, Antony (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/659,250

(22) Filed: Sep. 11, 2003

(65) Prior Publication Data

US 2004/0052772 A1 Mar. 18, 2004

Related U.S. Application Data

(62) Division of application No. 09/996,905, filed on Nov. 30, 2001, now Pat. No. 6,660,522, which is a division of application No. 09/556,124, filed on Apr. 20, 2000, now Pat. No. 6,605,466.

(30) Foreign Application Priority Data

Apr. 20, 1999 (FR) ............................................. 99 04970

(51) Int. Cl.$^7$ ............................ C12N 5/00; C12N 5/08; A61K 9/00
(52) U.S. Cl. ........................ 435/371; 435/1.1; 435/325; 435/366; 435/395; 435/372; 424/400; 424/93.7; 424/422; 424/444
(58) Field of Search ......................... 435/371, 1.1, 625, 435/366, 395, 372; 424/400, 93.7, 422, 444

(56) References Cited

U.S. PATENT DOCUMENTS

| 4,971,954 A | 11/1990 | Brodsky et al. |
| RE35,399 E | 12/1996 | Eisenberg |
| 5,861,153 A | 1/1999 | Schmidt et al. ............ 424/93.7 |
| 6,034,221 A | 3/2000 | Berenzenko et al. |

| 6,187,993 B1 | 2/2001 | Watt et al. |

FOREIGN PATENT DOCUMENTS

| EP | 0 462 426 A1 | 12/1991 |
| EP | 0 789 074 A1 | 8/1997 |
| WO | WO 92/10217 | 6/1992 |

OTHER PUBLICATIONS

G.M. Nemecek et al., "Safety Evaluation of Human Living Skin Equivalents", *Toxicologic Pathology*, vol. 27, No. 1, pp. 101–103, 1999.
K.M. Reiser et al., "Nonenzymatic Glycation of Type I Collagen", *The Journal of Biological Chemistry*, vol. 267, No. 34, Dec. 6, 1992, pp. 24207–24216.
M. Démarchez et al., "Migration of Langerhans Cells into Human Epidermis of 'Reconstructed' Skin, Normal Skin, or Healing Skin, After Grafting onto the Nude Mouse", *The Journal of Investigative Dermatology*, vol. 100, No. 5, May 1993, pp. 648–652.
M. Oimomi et al., "The Effect of Fructose on Collagen Glycation", *Kobe J. Med. Sci. 35*, Aug., 1989, pp. 195–200.
J. Font et al., "A New Three–Dimensional Culture of Human Keratinocytes: Optimization of Differentiation", *Cell Biology and Toxicology*, 1994; 10: pp. 353–359.
S.W. Hendrix et al., "Differential Response of Basal Keratinocytes in a Human Skin Equivalent to Ultraviolet Irradiation", *Arch. Dermatol. Res.* (1998) 290:420–424.
"Skin Aging", 1995–2001, http://www.lef.org/magazine/mag2001_report_carnosine 2_2.html.

*Primary Examiner*—Leon B. Lankford, Jr.
*Assistant Examiner*—Ruth A. Davis
(74) *Attorney, Agent, or Firm*—Burns, Doane, Swecker & Mathis, L.L.P.

(57) ABSTRACT

An aged skin equivalent comprising an epidermis equivalent and an aged dermis equivalent, wherein the aged dermis equivalent comprises glycated collagen.

An aged dermis equivalent, the epidermis equivalent obtained and methods of producing the aged skin and/or aged dermis equivalent and/or the epidermis equivalent.

40 Claims, 1 Drawing Sheet

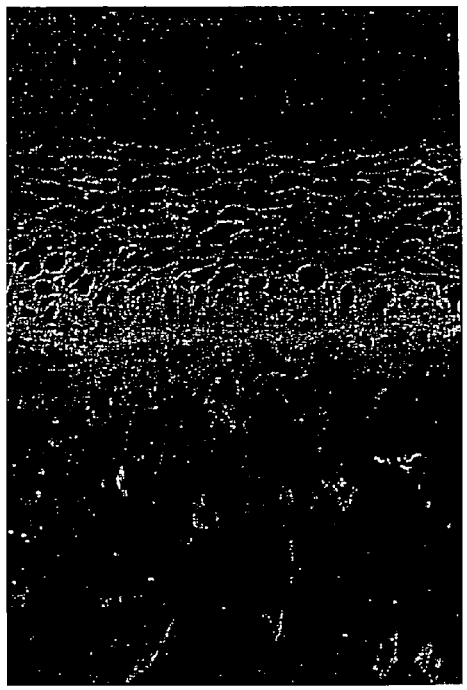
PHOTO 1
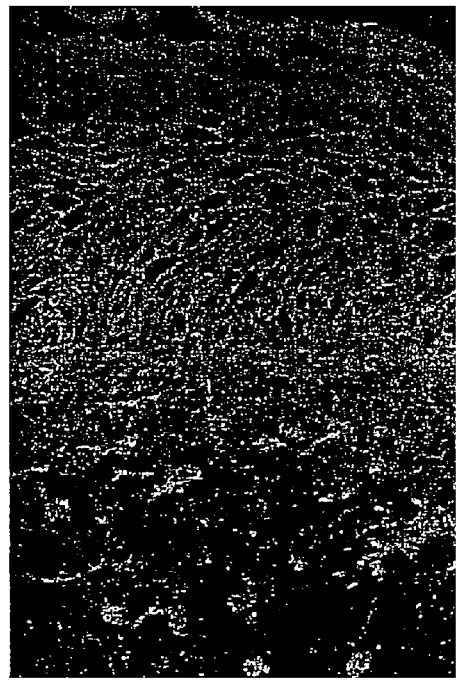
PHOTO 2

EPIDERMIS/DERMIS EQUIVALENTS AND AGED SKIN EQUIVALENTS SHAPED THEREFROM

CROSS-REFERENCE TO PRIORITY APPLICATION

This application is a divisional of application Ser. No. 09/996,905, filed on Nov. 30, 2001, now U.S. Pat. No. 6,660,522 which is a divisional of application Ser. No. 09/556,124, filed Apr. 20, 2000, now U.S. Pat. No. 6,605,466. The content of these related applications are hereby expressly incorporated by reference. This application claims priority under 35 U.S.C. §119 of FR-99/04970, filed Apr. 20, 1999, hereby expressly incorporated by reference.

BACKGROUND OF THE INVENTION

1. Technical Field of the Invention

The present invention relates to novel skin equivalents, to a method for the production thereof and to the epidermis equivalents and dermis equivalents comprising such novel skin equivalents (themselves per se novel).

2. Description of the Prior Art

For several years, the perfection of models of reconstructed skin which permit conducting studies required for a better understanding of the role of the skin in the mechanical domain and physiological domain has been ongoing.

Thus, models which more or less approximate human skin have been developed. Exemplary are the models described in EP-A-285471, EP-A-285474, EP-A-789074, EP-A-502172, EP-A-418035, WO-A-9116010, EP-A-197090, EP-A-20753, FR-A-2665175 and FR-A-2689904.

Very generally, the models of reconstructed skin described in the aforesaid publications comprise human keratinocytes associated or otherwise with other skin cells such as melanocytes and/or Langerhans cells, deposited onto a support, often a dermis equivalent, and cultured under conditions such that they commence a program of differentiation which results in the formation of an epidermis equivalent.

The dermis equivalents described to date are either artificial membranes such as, for example, Millipore filters, collagen-based subcutaneous substitutes, plastic or any other support which is compatible with cell viability, or supports which are more developed such as to approximate natural dermis, for example previously de-epidermilized dermis or collagen/fibroblast mixed lattices.

In the collagen/fibroblast mixed lattices the association of native collagen and isolated human fibroblasts ultimately provides a dermis equivalent which mimics a dermis which has not been subjected to the actions of the weather.

The protocols employed for the preparation of said lattices use collagen originating in general from young tissues, this collagen having, however, been subjected to the important post-translational modifications which intervene in the complex but nevertheless normal processes of its biosynthesis, but not having undergone all of the modifications which can intervene, in particular, during aging.

It is known to this art, in particular, to this art, that during aging and during the progress of certain diseases such as diabetes, non-enzymatic processes operate which involve an ose (glucose or ribose) which reacts according to the Maillard reaction with an amino group (for example a lysine residue) of the collagen to form a Schiff's base. This base, after undergoing an Amadori molecular rearrangement, may provide, by a succession of reactions, intramolecular bridging such as, for example, of pentosidine type. This phenomenon, termed glycation of collagen, increases uniformly with age, leading to a uniform increase in the glycation-product content of the skin. These glycation products include, for example, pyrraline, carboxymethyl lysine, pentosidine, crosslines, $N^{\epsilon}$-(2 carboxyethyl) lysine (CEL), glyoxal-lysine dimer (GOLD), methylglyoxal-lysine dimer (MOLD), 3DG-ARG imidazolone, versperlysines A, B, C, threosidine or, alternatively, advanced glycosylation end products or AGEs. This phenomenon is amplified in certain disease states, such as, for example, diabetes.

Without wishing to be bound to any particular theory as regards aging of the skin, it should be noted that other characteristics which might also be a consequence of these glycation phenomena, such as a decrease in heat denaturation, an increase in resistance to enzymatic digestion and an increase in intermolecular bridging, have been demonstrated during aging of the skin (Tanaka S. et al., 1988, *J. Mol. Biol.*, 203, 495–505; Takahashi M. et al., 1995, *Analytical Biochemistry*, 232, 158–162). In addition, modifications due to the glycation of certain constituents of the basal membrane such as collagen IV, laminine and fibronectin have been demonstrated (Tarsio J F. et al., 1985, *Diabetes*, 34, 477–484; Tarsio J F. et al., 1988, *Diabetes*, 37, 532–539; Sternberg M. et al., 1995, *C.R. Soc. Biol.*, 189, 967–985).

Thus, it is understood that during aging of the skin the physicochemical properties of collagen are modified and such collagen becomes more difficult to dissolve and more difficult to degrade.

Thus, one of the components of aged skin indeed appears to be glycated collagen.

It is also very well known that the skin constitutes a close association between at least two components thereof, i.e., the epidermis and the dermis. The interactions between the dermis and the eipdermis are such that it is reasonable to consider that a modification of one may have consequences on the other. It may be suspected that the aging of the dermis, in particular with its glycation phenomena, can only have consequences for the epidermis to which it is associated. Thus, during skin aging, the glycation of the collagen must promote modifications of the epidermis which must participate in the aging of the epidermis.

In this respect, it has now been demonstrated that a constitutive protein of normal epidermis, i.e., the β1 type integrin, an extracellular matrix receptor (see Ruoslahti E., 1991, *Cell Biology of Extracellular Matrix*, Plenum press New York, 343363), shows a distribution of its expression in aged epidermis which is very different from that in young epidermis. Specifically, while in a young epidermis, i.e., for the purposes of this invention an epidermis from a young subject, this protein is expressed in the very deep layers of the epidermis, i.e., up to a maximum of the second suprabasal layer, the situation is completely different in an aged epidermis, i.e., for the purposes of this invention in an epidermis from an elderly subject, where this protein is expressed in most layers of the epidermis, directly through to the last suprabasal layers under the cornified layer.

To date, no model of reconstructed skin in vitro is capable, either because of the protocols of preparation technique, or the simple fact that once reconstituted it does not undergo modification, of producing a skin equivalent at least one of the constituents of which provides one of the components of skin aging. Thus, no model of reconstructed skin in vitro presents the properties of an aged skin or permits the study of the processes resulting therein, or the study of the compounds and/or compositions which would at least make it possible to slow down or retard this/these process(es). The only known evaluations of these phenomena entail in vivo studies, either in animals or humans. Most particularly, for ethical reasons, the advantage of having such a model is conspicuously apparent.

Studies on glycation are known in the prior art. For example, a method is described for obtaining a connective tissue equivalent in the form of a lattice of glycated collagen and fibroblasts (see in this respect Frey et al. (1992, *C.R. Soc. Biol.*, 187, 223–231). However, not only have Frey et al. never investigated or even suggested the possibility of preparing a skin equivalent from their lattice, they have never compared this lattice to any dermis equivalent. In addition, but while recognizing the validity of the conjunctive tissue model of Frey et al., it will be appreciated that the protocol employed cannot provide the objectives established hereby, i.e., to reproduce in vitro a skin, and consequently an epidermis and a dermis, which has all or part of the properties of an aged skin.

By incubating the collagen and sugar for 9 hours at a temperature of 4° C., Frey et al. initiate the collagen glycation reaction, this reaction then continuing in the lattice in which the collagen is in this manner preglycated. If it is desired to attain a sufficient level of glycation, such as to mimic an aged skin, it is then necessary to permit the glycation reaction to continue in the lattice formed in this fashion, i.e., in the process of contraction, for a further time which is sufficient to attain the desired level. However, those skilled in this art are cognizant that to establish an epidermis equivalent containing at least keratinocytes on a dermis equivalent of collagen/fibroblast lattice type, the seeding of the keratinocytes must be conducted onto a lattice which cannot have exceeded a determined stage of contraction. It will thus be seen, therefore, that it is not possible to obtain by the Frey protocol a dermis equivalent which mimics an aged or very aged dermis, i.e., highly or very highly glycated.

SUMMARY OF THE INVENTION

Accordingly, a major object of the present invention is the provision of a skin equivalent which comprises an epidermis equivalent produced on an aged dermis equivalent, particularly on a lattice comprising at least glycated collagen and fibroblasts.

A significant advantage of this invention is providing a model of reconstructed skin in which at least one of the components thereof would have one of the aspects of an aged skin.

DETAILED DESCRIPTION OF BEST MODE AND SPECIFIC/PREFERRED EMBODIMENTS OF THE INVENTION

More particularly according to the present invention, the assignee hereof has long been interested in the production of in vitro models of reconstructed skin, and a novel model of reconstructed skin has now been developed comprising an epidermis equivalent and a dermis equivalent, said dermis equivalent comprising an aged dermis equivalent, particularly a lattice which comprises at least glycated collagen and fibroblasts.

Thus, the present invention features a novel aged dermis equivalent, comprising at least glycated collagen and fibroblasts.

Different techniques for tracking the formation of the glycation products are described in the prior art. In this respect, methods which are representative are described by Cefalu W. T. et al. (*Journal of Gerontology; Biological Sciences*, 1995, vol. 50 A, No. 6, 13337–13341), by Sell D. R. (*Diabetes/Metabolism*, 1991, vol. 7, No. 4, 239–251), by Miyata T. et al. (*Journal of the American Society of Nephrology*, 1996, vol. 7, No. 8, 1198–1206), or, alternatively, by Furth A. J. (*Analytical Biochemistry*, 1991, 192, 109–111).

Thus, it is possible to measure the level of glycating compound bound to the collagen and/or the level of glycating compound remaining after the reaction. As described above, the glycation of collagen leads to the formation of glycation products such as, for example, pyrraline, carboxymethyl-lysine, pentosidine, crosslines, $N^\epsilon$-(2-carboxyethyl)lysine (CEL), glyoxal-lysine dimer (GOLD), methylglyoxal-lysine dimer (MOLD), 3DG-ARG imidazolone, versperlysines A, B and C, threosidine or alternatively advanced glycosylation end products or AGEs.

Certain of these glycation products have the particular feature of emitting a measurable fluorescence after excitation. For example, pentosidine, when excited at a wavelength ($\lambda$ex) of 328 nm, emits a fluorescence at a wavelength ($\lambda$em) of 378 nm. Similarly, AGEs, when excited at a wavelength ($\lambda$ex) of 370 nm, emit a fluorescence at a wavelength ($\lambda$em) of 440 nm. The ratio of the fluorescence which is emitted by a given glycation product in the dermis equivalent comprising at least glycated collagen and fibroblasts to the fluorescence which is emitted by the same glycation product in a control dermis equivalent comprising at least non-glycated collagen and fibroblasts, measured under the same experimental conditions, makes it possible to characterize the level of glycation of the aged dermis equivalent.

Particularly, according to the invention, the fluorescence of the pentosidine and/or the AGEs is measured both in the aged dermis equivalent comprising glycated collagen and in a control comprising non-glycated collagen.

Thus, according to the invention, the aged dermis equivalent has a level of glycation ranging from 2 to 30 and particularly from 8 to 18.

Consistent herewith, the collagen may be any type of collagen of any origin. In this respect, reference is made to the different types of collagen noted in the reviews of Van der Rest and Garonne, 1990, *Biochem.*, vol. 72, 473–484 or, alternatively, 1991, *Faseb Journal*, vol. 5, 2814–2823. Thus, according to the invention, the collagen is preferably selected from among the fibrillary collagens of type I, III or V.

Preferably, collagen of animal origin is used, particularly collagen of bovine origin.

The preferred collagen according to the invention is type I collagen. Very preferably, type I bovine collagen is employed.

It will of course be appreciated that a mixture of collagen of different types in any proportion and/or of different origins may be used.

Also according to the invention, the fibroblasts may emanate from any origin, but are preferably fibroblasts of human origin. They may be prepared according to any known technique of the prior art, for example by mechanical and/or enzymatic dissociation of the macromolecules of the extracellular matrix of the dermis or by growth of fibroblasts from explants.

Too, the dermis equivalent of the invention comprises at least glycated collagen and fibroblasts, but may also contain any other component that might be advantageous to introduce therein such as, for example, endothelial cells, macrophages or alternatively nerve cells.

The present invention also features an epidermis equivalent comprising at least keratinocytes, characterized in that it can be formed by seeding at least keratinocytes onto a dermis equivalent comprising at least glycated collagen and fibroblasts.

As above indicated, depending on age, certain markers of the eipdermis could undergo modifications either in their quantity or in the localization of their expression. Particularly, it has been shown that the expression of β1 integrin in the epidermis is modified in its localization with the age of the epidermis. Specifically, while in a young epidermis this protein is expressed strictly in a maximum of the first two suprabasal layers, with age this expression, while conserving its localization in the first two suprabasal layers, appears in layers which are more and more superficial to the point of appearing in all of the suprabasal layers including the final layers adjoining the stratum corneum.

Thus, in one embodiment of the invention the epidermis equivalent is characterized in that it has modified expression of β1 integrin, particularly expression of β1 integrin in the cells of at least the first three suprabasal layers.

Very preferably, according to the invention, the epidermis equivalent comprising at least keratinocytes is characterized in that it has modified expression of β1 integrin, particularly expression of β1 integrin in the cells of at least the first three suprabasal layers, and in that it is obtained by seeding at least keratinocytes onto a dermis equivalent comprising at least glycated collagen and fibroblasts.

Of course, any method which makes it possible to demonstrate the expression of β1 integrin can be used to characterize the epidermis of the invention. Labelling with the aid of anti-β1 integrin antibodies is exemplary.

The keratinocytes used according to the invention may emanate from any origin, but are preferably keratinocytes of human origin. They may be prepared according to any known method of the prior art. Culturing from dissociated epidermis originating from a normal skin sample, or the culturing of keratinocytes derived from the sheath of the hair follicles, are representative examples.

Preferably, keratinocytes from normal human skin are used.

Also, preferably, the keratinocytes are prepared from dissociated human epidermis originating from a normal human skin sample according to the technique described in Régnier et al., *Frontier of Matrix Biology*, Vol. 9, 4–35 (Karger, Basle 1981).

The epidermis equivalent of the invention comprises at least keratinocytes, but it may comprise any other cell type which might be incorporated therein such as, for example, Langerhans cells and/or precursors of Langerhans cells and/or melanocytes.

Of course, the skin equivalent which has the best similarity with normal skin is the skin equivalent which contains the three essential cell types present in normal skin.

Thus, advantageously the model of reconstructed skin according to the invention comprises, in addition, melanocytes and/or Langerhans cells and/or precursors of Langerhans cells.

The melanocytes according to the invention may be isolated from any organ which contains them such as, for example, normal skin or hair follicles.

Preferably, melanocytes isolated from normal skin are used.

Any known method of preparation of melanocytes of the prior art may be used according to the invention. The method described in Olsson et al., *Acta Derm. Venereol.*, 1994, 74, 226–268, is one such example.

The Langerhans cells and/or the precursors of Langerhans cells which can be employed according to the invention may be as described in European Patent Application published under the number EP-A-789074, assigned to the assignee hereof.

This invention also features an aged skin equivalent, which comprises at least one epidermis equivalent and one aged dermis equivalent.

In another embodiment of the invention, the aged skin equivalent comprises an aged dermis equivalent as described above.

In another embodiment of the invention, the aged skin equivalent comprises an epidermis equivalent as described above.

An aged skin equivalent which is very preferable according to the invention comprises an epidermis equivalent comprising at least keratinocytes which have modified expression of β1 integrin, particularly expression of β1 integrin in the cells of at least the first three suprabasal layers and is characterized in that it can be obtained by seeding at least keratinocytes onto an aged dermis equivalent comprising at least glycated collagen and fibroblasts, said aged dermis equivalent having a level of glycation ranging from 2 to 30, and particularly from 8 to 18.

The present invention also features a method for preparing an aged skin equivalent comprising an epidermis equivalent and a dermis equivalent which itself comprises a lattice comprising at least glycated collagen and fibroblasts, wherein a first step a lattice comprising at least glycated collagen and fibroblast is prepared and in a second step an epidermis equivalent comprising at least keratinocytes is reconstituted on the lattice obtained in the first step.

The first step may be carried out by any known technique of the prior art, provided that the collagen may be glycated either beforehand, during or after the formation of the lattice. Preferably, according to the invention, a lattice is prepared in which either collagen which is glycated prior to the formation of the lattice is used or a glycation agent is added to the mixture of collagen and fibroblast which is used, in order to effect the glycation either during the preparation of the lattice or after formation of the lattice.

Preferably, the lattice is prepared using previously glycated collagen.

Also preferably, the lattice is prepared according to the method described by Asselineau et al., 1987, (*Models in Dermato.*, vol. III, Ed. Lowe & Maibach, 1–7) using preglycated collagen.

Any known method of glycation may be used to produce glycated collagen. For example, the methods described by Tanaka et al. (*J. Mol. Biol.*, 1988, 203, 495–505), Tarsio J F. et al. (1985, *Diabetes,* 34, 477–484), Tarsio J F. et al. (1988, *Diabetes,* 37, 532–539) or, alternatively, by Frey J. et al. (1992, *C.R. Soc. Biol.,* 187, 223–231) are exemplary thereof.

Preferably, the glycation may be carried out by contacting a solution of at least one collagen with a solution of at least one glycating agent in such manner as to induce the glycation reaction of the collagen in vitro in the absence of cells.

As indicated above, the collagen may be any type of collagen, of any origin, alone or in admixture.

Preferably, the collagen is of animal origin, particularly collagen of bovine origin.

The preferred collagen according to the invention is type I collagen. Very preferably, type I bovine collagen is employed.

The collagen solution is advantageously at a concentration of from 2 mg/ml to 6 mg/ml and preferably from 3 mg/ml to 5 mg/ml.

The glycating agent may be any agent which enables the glycation, i.e., which is capable of reacting according to the Maillard reaction with an amino group of the collagen to form a Schiff's base. In this respect, exemplary intermediates of the Maillard reaction include for example, glucosone, 3-deoxyglucosone, glyoxal, methylglyoxal or, alternatively, sugars.

Any type of sugar can be used according to the invention, whether it is in monomeric or polymeric form. According to the invention, a monomeric sugar is preferred.

By "sugar" are intended compounds which possess several alcohol groups and at least one aldehyde group. Oses are particularly representative thereof.

Among the sugars which are suitable according to the invention, ribose, fructose or glucose, inter alia, are exemplary. Preferably, ribose or glucose is used.

The sugar may be in any one of the dextrorotatory or laevorotatory conformations. Preferably, a sugar in dextrorotatory conformation is used.

Particularly, according to the invention D-fructose, D-ribose or D-glucose is used. Preferably D-ribose or D-glucose is used.

The glycating agent may be used either alone or in admixture.

The amount of glycating agent which can be used according to the invention should be sufficient to permit initiating the non-enzymatic reactions which lead to the formation of Schiff's base. It should be understood that varying this amount makes it possible to obtain a final product, the glycated collagen, whose level of glycation varies from relatively unglycated to very highly glycated. Thus, the amount of glycating agent advantageously ranges from 0.5% to 20%, preferably from 1% to 10% by weight of the total weight of the collagen solution.

The glycation reaction is carried out at a temperature which is close to room temperature. Thus, the reaction is carried out at a temperature ranging from 15° C. to 30° C., preferably from 20° C. to 25° C.

The duration of the glycation reaction depends on the desired level of glycation. It will be appreciated that the longer the time the higher the level of glycation. Thus, the duration of the glycation reaction advantageously ranges from 15 days to 2 months, preferably from 25 days to 35 days.

When it is determined to carry out the glycation prior to the preparation of the lattice, it is possible to subject the glycated collagen to all the subsequent steps necessary for producing the purest possible product. Thus, it is possible to attempt to eliminate any trace of glycating agent which would not have reacted during the reaction. For this any known technique may be employed. For example, the preglycated collagen solution is subjected to a series of dialyses against water and/or acetic acid.

In another embodiment of the invention, the "preglycated" collagen solution obtained may be mixed with native collagen before use for the preparation of the dermis equivalent. In this instance, the ratio of glycated collagen to non-glycated collagen may range from 25 to 75 and preferably from 45 to 55. Variation of this ratio makes it possible to modulate the level of glycation of the lattice. Preferably, according to the invention a mixture of glycated collagen and non-glycated collagen is used, and even more preferably a mixture of glycated collagen and non-glycated collagen in a 50/50 ratio.

The second step of the method of the invention may be carried out by any known technique of the prior art.

In this respect, techniques which are representative are described in EP-A-285471, EP-A-285474, EP-A-789074, EP-A-502172, EP-A-418035, WO-A-9116010, EP-A-197090, EP-A-20753, FR-A-2665175 and FR-A-2689904, or, alternatively, that described by Asselineau et al., 1985, (*Exp. Cel. Res.*, 536–539) and 1987, (*Models in Dermato.*, vol. III, Ed. Lowe & Maibach, 1–7).

Preferably, the method described by Asselineau and colleague is employed.

The keratinocytes according to the invention may emanate from any origin, but are preferably keratinocytes of human origin. They may be prepared according to any known procedure of the prior art. Culture from dissociated epidermis originating from a normal skin sample, or the culture of keratinocytes derived from the sheath of hair follicles, are representative.

Preferably, the keratinocytes are prepared from dissociated human epidermis originating from a normal human skin sample according to the method described in Regnier et al., *Frontier of Matrix Biology*, Vol. 9, 4–35 (Karger, Basle 1981).

Advantageously, after seeding the keratinocytes onto the support, the culture may be maintained submerged in a nutritive medium which may be, for example, the medium described by Rheinwald and Green, 1975, (*Cell*, 6, (3), 317–330), this medium allowing the proliferation of the keratinocytes (referred to hereinafter as medium 3F).

After an incubation time of 3 to 15 days, preferably of 7 to 9 days, the skin equivalent is maintained at the air/liquid interface by, for example, depositing it onto a metal grid. The liquid then preferably consists of the same nutritive medium as the previous one.

The incubation then continues until production of a skin equivalent having the properties of a skin, i.e., the support on which is an epidermis equivalent having the four conventional types of cell layer, i.e., the basal, suprabasal, granular and cornified layers.

Thus, the incubation continues for a duration advantageously ranging from 5 days to 30 days, preferably from 7 days to 10 days.

The model of reconstructed skin produced in this manner comprises two entities: the support and the epidermis equivalent, that it is possible to physically separate from each other.

The epidermis equivalent may thus be used separately from the support.

As above indicated, to date no in vitro model of reconstructed skin had the properties of an aged skin or permitted the study of the processes resulting therein or the study of the compounds and/or compositions which would at least make it possible to modify the process thereof. The skin equivalent obtained according to the invention resolves these problems, since it has at least one of the properties of aged skin, i.e., a glycated collagen. This important property which the model and method thereof make it possible to vary in any proportion, permits the study of the glycation phenomenon in itself and modulators (inhibitors or activators) of this phenomenon, the study of phenomena linked to aged skin such as, for example, wrinkles, the study of modulators (isolated compounds and/or compositions) of the appearance of the wrinkles (particularly the inhibitors), the study of photoaging and the effect on the skin of ultraviolet rays, as well as modulators of these effects (protective compounds and/or compositions, filters, etc.), the study of the influence of glycation on the components of the skin (bristles and/or hair, blood vessels, nerve fibers, etc.), and in the therapeutic domain the study of the complications caused by diabetes via glycation.

Thus, this invention also features employing an aged skin and/or aged dermis equivalent and/or an aged epidermis equivalent as described above for the study of the glycation phenomenon itself and modulators (inhibitors or activators) of this phenomenon, the study of phenomena linked to aged skin such as, for example, wrinkles, the study of modulators (isolated compounds and/or compositions) of the appearance of the wrinkles (particularly the inhibitors), the study of photoaging and the effect on the skin of ultraviolet rays as well as modulators of these effects (protective compounds and/or compositions, screening agents, etc.), the study of the influence of glycation on the components of the skin (bristles and/or hair, blood vessels, nerve fibers, etc.), and in the therapeutic domain the study of the complications caused by diabetes via glycation.

It will also been seen that, according to the invention, the epidermis equivalent which is reconstructed on the dermis equivalent comprising at least glycated collagen and fibroblasts may have a modified distribution of the expression of $\beta 1$ integrin. In this instance, if the variation in the distribution of this marker is linked to the age of the epidermis, it is conceivable to use the aged skin equivalent of the invention to evaluate any product able to treat aged skin by measuring its effect by the effect that it produces on the modification of the distribution of $\beta 1$ integrin expression in the epidermis equivalent.

FIG. 1 better illustrates the invention, without however limiting its scope. In this figure, the photographs show sections of skin equivalents after immunolabelling with the aid of an anti-$\beta 1$ integrin antibody. Photo 1 represents the immunolabelling of a skin equivalent comprising an epidermis equivalent reconstructed on a dermis equivalent which is prepared with non-glycated collagen. Photo 2 represents the immunolabelling of a skin equivalent comprising an epidermis equivalent reconstructed on a dermis equivalent which is prepared with glycated collagen according to the invention.

In order to further illustrate the present invention and the advantages thereof, the following specific examples are given, it being understood that same are intended only as illustrative and in nowise limitative.

EXAMPLES

Media and buffers unless otherwise indicated; all media and buffers used in the following examples are described in Bell et al., 1979, (*P.N.A.S. USA*, 76, 1274–1278), Asselineau and Prunieras, 1984, (*British J. of Derm.*, 111, 219–222) or Asselineau et al., 1987, (*Models in Dermato.*, vol. III, Ed. Lowe & Maibach, 1–7).

Example 1

Preparation of Glycated Bovine Collagen I:

10 ml of bovine collagen I solution at a concentration of 3 mg/ml, 0.8 ml of 0.5N sodium hydroxide to neutralize the acidic collagen solution and 100 µl of a 1M solution of D-ribose in water were placed into a 50 ml Falcon tube.

The tube, rendered opaque to the light, was placed horizontally and gently shaken at room temperature (25° C.) for 1 month.

At the end of the "preglycation", the solution was placed in dialysis tubing (Spectra/Poly labo 32 mm No. 132655/85716) and was subjected to a series of successive dialyses:

24 hours against demineralized water at 4° C. to eliminate the unbound sugar or the collagen degradation products;

7 days against 0.5N acetic acid to redissolve the collagen, in 2 baths of three and a half days;

3×24 h against 0.017N acetic acid with bath changing every day.

After the last dialysis, the contents of the dialysis tubing were recovered in a sterile beaker and the solution was transferred into a sterile 50 ml Falcon tube, rendered opaque to the light.

The "preglycated" collagen solution was then ready to use. It may be stored at 4° C.

Example 2

Preparation of an Aged Dermis Equivalent:

3.22 ml of 1.76×MEM medium, 0.63 ml of foetal calf serum, 0.35 ml of 0.1N sodium hydroxide and 0.20 ml of an MEM medium/Hepes mixture containing 10% foetal calf serum (MEM/Hepes/FCS10) were placed into a sterile Falcon tube.

0.50 ml of MEM medium/Hepes/FCS10 were then added containing fibroblasts derived from human mammary plastic surgery which were prepared beforehand according to the technique described by Bell et al., 1979, (*P.N.A.S. USA*, 76, 1274–1278), Asselineau and Prunieras, 1984, (*British J. of Derm.*, 111, 219–222) or Asselineau et al., 1987, (*Models in Dermato.*, vol. III, Ed. Lowe & Maibach, 1–7), at a concentration of 1×10⁶ cells for 0.5 ml of culture medium.

2 ml of a volume/volume mixture of preglycated collagen from Example 1 and non-glycated collagen having served in the preparation of the preglycated collagen from Example 1, at a concentration of 3 mg/ml in acetic acid at ¹⁄₁₀₀₀, was then slowly added, against the wall of the tube, in such manner as to observe the appearance of a whiteish cloud. The entire medium was then mixed cautiously and plated in a 60 mm diameter Petri dish (type Falcon 60 mm, ref. 1016). The Petri dish was then placed in an incubator at 37° C. and left for about 2 hours, 30 minutes. When the appearance of 2 phases (gel+medium) was observed, the lattice was cautiously dissociated from its support and the lattice dissociated from its support in this manner was left in the incubator for 4 days.

Example 3

Measurement of the Level of Glycation of the Aged Dermis Equivalent From Example 2:

In parallel to the production of the aged dermis equivalent of Example 2, a dermis equivalent without glycated collagen (but with non-glycated collagen) was produced. This equivalent was used as a control in the determination of the level of glycation of the glycated dermis equivalent from Example 2.

Two lattices (one aged, one control) prepared according to Example 2 were rinsed three times in phosphate buffered saline (PBS), then dried. The lattices were then placed in an Eppendorf tube and subjected to digestion with pepsin (Sigma P-6887) at 37° C. in a water bath overnight (12 hours) in a proportion of 500 µg of pepsin per lattice in 0.5 ml of 0.5N acetic acid.

515 µl of 0.5N sodium hydroxide were then added to each tube and the contents of each tube were filtered through a 0.22 µm spin filter (Sigma).

The fluorescence was then measured with the aid of a Hitachi spectrofluorimeter, model F2000. The fluorescence emitted by pentosidine at $\lambda$em=378 nm after excitation at $\lambda$ex=328 nm and the fluorescence emitted by AGEs at $\lambda$em=440 nm after excitation at $\lambda$ex=370 nm were thus measured.

The results obtained are reported in the Table below:

TABLE

|  | Pentosidine | AGEs |
| --- | --- | --- |
| Control | 650 | 430 |
| Glycated lattice | 6100 | 1820 |

In this example the level of glycation of the aged dermis equivalent was thus established at 9.4 for the pentosidine and at 4 for the AGEs.

Example 4

Preparation of an Aged Skin Equivalent:

An aged dermis equivalent as prepared in Example 2 was set up and well spread out in a Corning θ 60 mm culture dish on a droplet of collagen "glue" (0.6 ml), then maintained at 37° C. in an incubator for 20–30 minutes.

A sterile steel ring was placed on the lattice and 0.5 ml of a cellular suspension of human keratinocytes originating from mammary plastic surgery which were prepared according to Régnier et al., (*Frontier of Matrix Biology*, Vol. 9, 4–35, Karger, Basle 1981), in a proportion of 100,000 cells/ml in MEM medium 10% FCS+3F, were placed inside the ring. About 6 ml of medium (MEM 10% FCS+3F) were placed around the ring and the dish was placed in an incubator at 37° C. for 2 hours. The ring was then removed and the dish again placed in the incubator.

After 8 days, the culture was then placed at the air/liquid interface, said liquid consisting of the same medium as above.

The culturing was then continued for 1 week until production of an epidermis equivalent which was histologically satisfactory, i.e., an epidermis equivalent which had the four conventional cell layers, i.e., the basal, suprabasal, granular and cornified layers.

Example 5

Characterization of the Expression of β1 Integrin in the Epidermis Equivalent Obtained in Example 4:

The expression of β1 integrin in the epidermis equivalent obtained in Example 4 was observed after immunolabelling with the aid of a mouse monoclonal antibody directed against β1 integrin (Immunotech, Marseille, France, Cat. 1151): After freezing, the skin equivalents obtained in Example 4 were sectioned into 5 µm thick slices with the aid of a cryostat (make/model). The sections were then rinsed twice with PBS and 25 µl of anti-β1 integrin antibody diluted at 1/50(Immunotech, Marseille, France, Cat5. 1151) were deposited onto each section and left for 30 minutes at room temperature (25° C.). The sections were then rinsed twice with PBS and 25 µl of FITC conjugated antibody (rabbit anti mouse FITC, Dako F232) were deposited onto each section and left for 30 minutes at room temperature (25° C.). The sections were rinsed twice with PBS and observed, after mounting, under a LEICA fluorescence microscope, model LEITZ DMRB.

Observation indicated that in the control the β1 integrin was expressed in the basal layer of the epidermis reconstructed on the non-glycated dermis equivalent and in the first suprabasal layer (FIG. 1, photo 1), whereas it was expressed in all of the suprabasal layers, up to just under the stratum corneum, in the epidermis reconstructed on the aged dermis equivalent (FIG. 1, photo 2).

These results correlate with the observation of a distribution in vivo of the expression of the β1 integrin in the basal layer and first suprabasal layer in a young subject's skin, and in the basal layer and at least the first 3 suprabasal layers in the skin of an elderly individual.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An epidermis equivalent comprising at least keratinocytes, said epidermis equivalent being obtained by seeding of at least keratinocytes onto a dermis equivalent comprising at least glycated collagen and fibroblasts, wherein said dermis equivalent has a level of glycation from 2–30 times that of a control dermis comprising collagen not subjected to a glycation process and fibroblasts.

2. The epidermis equivalent of claim 1, wherein said epidermis equivalent has a modified distribution of expression of β1 integrin.

3. The epidermis equivalent of claim 2, wherein the modified distribution of expression is expression of β1 integrin in the cells of at least the first three suprabasal layers.

4. The epidermis equivalent of claim 1, wherein the keratinocytes comprise keratinocytes of human origin.

5. The epidermis equivalent of claim 1, further comprising melanocytes and/or Langerhans cells and/or precursors of Langerhans cells.

6. The epidermis equivalent of claim 1, wherein said dermis equivalent has a level of glycation from 8 to 18 compared to a control dermis.

7. The epidermis equivalent of claim 1, wherein the glycated collagen comprises collagen of animal or human origin.

8. The epidermis equivalent of claim 1, wherein the glycated collagen comprises collagen of bovine origin.

9. The epidermis equivalent of claim 1, wherein the glycated collagen comprises type I collagen.

10. The epidermis equivalent of claim 1, wherein the fibroblasts comprise fibroblasts of human origin.

11. An epidermis equivalent comprising at least keratinocytes, said epidermis equivalent having a modified distribution of expression of β1 integrin, said epidermis equivalent being obtained by seeding of at least keratinocytes onto an aged dermis equivalent comprising at least glycated collagen and fibroblasts.

12. The epidermis equivalent of claim 11, wherein the modified distribution of expression is expression of β1 integrin in the cells of at least the first three suprabasal layers.

13. The epidermis equivalent of claim 11, wherein the keratinocytes comprise keratinocytes of human origin.

14. The epidermis equivalent of claim 11, further comprising melanocytes and/or Langerhans cells and/or precursors of Langerhans cells.

15. The epidermis equivalent of claim 11, wherein the aged dermis equivalent has a level of glycation from 2–30 times that of a control dermis comprising collagen not subjected to the glycation process and fibroblasts.

16. The epidermis equivalent of claim 15, wherein said aged dermis equivalent has a level of glycation from 8 to 18 compared to a control dermis.

17. The epidermis equivalent of claim 11, wherein the glycated collagen comprises collagen of animal or human origin.

18. The epidermis equivalent of claim 11, wherein the glycated collagen comprises collagen of bovine origin.

19. The epidermis equivalent of claim 11, wherein the glycated collagen comprises type I collagen.

20. The epidermis equivalent of claim 11, wherein the fibroblasts comprise fibroblasts of human origin.

21. A method for obtaining an epidermis equivalent according to claim 1, comprising seeding keratinocytes onto an aged dermis equivalent, wherein the aged dermis equivalent comprises at least glycated collagen and fibroblasts and wherein the aged dermis equivalent has a level of glycation from 2–30 times that of a control dermis comprising collagen not subjected to the glycation process and fibroblasts.

22. The method of claim 21, comprising at least keratinocytes, said epidermis equivalent having a modified distribution of expression of $\beta 1$ integrin.

23. The method of claim 22, wherein the modified distribution of expression is expression of $\beta 1$ integrin in the cells of at least the first three suprabasal layers.

24. The method of claim 21, wherein the keratinocytes comprise keratinocytes of human origin.

25. The method of claim 21, further comprising melanocytes and/or Langerhans cells and/or precursors of Langerhans cells.

26. The method of claim 21, wherein said aged dermis equivalent has a level of glycation from 8 to 18 compared to a control dermis.

27. The method of claim 21, wherein the glycated collagen comprises collagen of animal or human origin.

28. The method of claim 21, wherein the glycated collagen comprises collagen of bovine origin.

29. The method of claim 21, wherein the glycated collagen comprises type I collagen.

30. The method of claim 21, wherein the fibroblasts comprise fibroblasts of human origin.

31. A method for obtaining an epidermis equivalent having a modified distribution of $\beta 1$ integrin expression according to claim 11, comprising constructing an epidermis equivalent by seeding at least keratinocytes on an aged dermis equivalent comprising at least collagen and fibroblasts to induce a modified distribution of $\beta 1$ integrin expression.

32. The method of claim 31, wherein the modified distribution of expression is expression of $\beta 1$ integrin in the cells of at least the first three suprabasal layers.

33. The method of claim 31, wherein the keratinocytes comprise keratinocytes of human origin.

34. The method of claim 31, further comprising melanocytes and/or Langerhans cells and/or precursors of Langerhans cells.

35. The method of claim 31, wherein the aged dermis equivalent has a level of glycation from 2–30 times that of a control dermis comprising collagen not subjected to the glycation process and fibroblasts.

36. The method of claim 35, wherein said aged dermis equivalent has a level of glycation from 8 to 18 compared to a control dermis.

37. The method of claim 31, wherein the glycated collagen comprises collagen of animal or human origin.

38. The method of claim 31, wherein the glycated collagen comprises collagen of bovine origin.

39. The method of claim 31, wherein the glycated collagen comprises type I collagen.

40. The method of claim 31, wherein the fibroblasts comprise fibroblasts of human origin.

* * * * *